United States Patent [19]

Weigert

[11] Patent Number: 5,216,152
[45] Date of Patent: Jun. 1, 1993

[54] PROCESS FOR THE CATALYTIC PYROLYSIS OF BIS(HEXAMETHYLENE)TRIAMINE

[75] Inventor: Frank J. Weigert, Wilmington, Del.

[73] Assignee: E. I. du Pont de Nemours and Company, Wilmington, Del.

[21] Appl. No.: 869,972

[22] Filed: Apr. 16, 1992

[51] Int. Cl.$^5$ .......................................... C07D 295/02
[52] U.S. Cl. .................................... 540/612; 564/511
[58] Field of Search ........................ 564/511; 540/612

[56] References Cited

U.S. PATENT DOCUMENTS

| | | | |
|---|---|---|---|
| 4,001,213 | 1/1977 | Hershman et al. | 260/239 |
| 4,247,481 | 1/1981 | Campbell et al. | 564/492 |
| 4,906,783 | 3/1990 | Smiley | 564/492 |
| 4,937,336 | 6/1990 | Atadan | 540/612 |

FOREIGN PATENT DOCUMENTS 423526  4/1991  European Pat. Off. ............ 540/612

OTHER PUBLICATIONS

Mikhailova et al., *Zh. Prikl. Khim.*, 47(8) 1790-1794 (1974).
Murahashi et al., *J. Am. Chem. Soc.*, 105, 5002-5011 (1983).
Cooper et al., *Chemtech*, 378-383, Jun., 1991.

*Primary Examiner*—Floyd D. Higel

[57] ABSTRACT

The catalytic pyrolysis of bis(hexamethylene)-triamine in a slurry or fixed bed reaction yields hexamethyleneimine, hexamethylenediamine and N-(6-aminohexyl)-hexamethyleneimine.

14 Claims, No Drawings

PROCESS FOR THE CATALYTIC PYROLYSIS OF BIS(HEXAMETHYLENE)TRIAMINE

This invention relates to the preparation of hexamethyleneimine, hexamethylenediamine, and N-(6-aminohexyl)hexamethyleneimine, by the catalytic pyrolysis of bis(hexamethylene)triamine.

The preparation of hexamethyleneimine by the catalytic reaction of 1,6-hexamethylenediamine and hydrogen in the vapor phase is described in U.S. Pat. No. 4,001,213. The preferred catalysts disclosed are nickel, copper, cobalt, and iron, but noble metals of Group 8, i.e., rhodium, palladium, and platinum catalysts, are also disclosed. Example 6 of this patent shows a catalyst of palladium and cobalt. The example concludes with the statement, "While palladium increased the activity of the catalyst system it drastically reduces the selectively to the desired imine product."

U.S. Pat. No. 4,937,336 of Atadan of Jun. 26, 1990 discloses the preparation of hexamethyleneimine by the catalytic reaction of 1,6-hexamethyleneamine and hydrogen in the vapor phase. A solid palladium metal catalyst on an inert support is used.

Mikhailova, T. A., et al., Zh. Prikl. Khim. (Leningrad), 47(8), 1790-4, 1974 (English translation), describe the preparation of piperazine by cyclization of diethylenetriamine on a nickel hydrogenation catalyst in the presence of ammonia.

Murahashi, S. I., et al., J. Am. Chem. Soc., 105, 5002-11, 1983, describe the preparation of triamines by the palladium catalyzed reaction of diamines with cyclic amines.

European Patent Application 423 526 2A discloses preparation of triethylenediamine and piperazine from ethylenediamine. The reaction was catalyzed with alkali metal or metal-exchanged zeolite.

Cooper, C. A., et al., CHEMTECH, 378-383, June 1991, discuss the nickel-catalyzed reaction of an alcohol $RCH_2OH$ or an amine $RCH_2NH_2$ with $R'_2NH$, which represents ammonia or any primary or secondary amine, to form $RCH_2NR'_2$. The implication is that tertiary amines do not undergo this reaction.

Bis(hexamethylene)triamine is a byproduct from the manufacture of hexamethylenediamine and may also be prepared by methods well known in the art, e.g., from 6-aminohexanenitrile, as disclosed in U.S. Pat. No. 4,906,783 of Smiley issued Mar. 6, 1990.

SUMMARY OF THE INVENTION

The present invention provides a process for the preparation of hexamethyleneimine, hexamethylenediamine, and N-(6-aminohexyl)hexamethyleneimine comprising pyrolyzing bis(hexamethylene)triamine in the presence of a catalyst comprising palladium, platinum, ruthenium, iridium, rhodium, nickel, or mixtures thereof, on a support. In one aspect the present invention provides a process for the preparation of hexamethyleneimine (HMI), hexamethylenediamine (HMD), and N-(6-aminohexyl)-hexamethyleneimine (AHI) by a fixed bed reaction comprising heating bis(hexamethylene)triamine in the presence of a catalyst comprising palladium, platinum, ruthenium, iridium, rhodium, nickel, or mixtures thereof, on a support. In a further aspect, the present invention provides a process for the preparation of hexamethyleneimine (HMI), hexamethylenediamine (HMD) and N-(6-aminohexyl)-hexamethyleneimine (AHI) by a slurry reaction comprising heating bis(hexamethylene)triamine (BHMT) in the presence of a catalyst comprising palladium, platinum, ruthenium, iridium, rhodium, nickel, or mixtures thereof, on a support or in the presence of a catalyst comprising unsupported palladium black.

DETAILED DESCRIPTION OF THE INVENTION

In the process for the preparation of HMI, HMD, and AHI, BHMT is passed through a fixed-bed reactor filled with a supported metal catalyst. Suitable operating temperatures range from about 100° C. to about 250° C., with the preferred range being from about 175° C. to about 225° C. Pressures suitable for use herein are from about 1 to about 70 atm ($1 \times 10^5$ to $7 \times 10^6$ Pascals). The contact time typically ranges from about 0.1 seconds to about 5 minutes. The preferred contact time is from about 10 to 60 seconds.

If desired, the BHMT stream may also contain non-interfering solvents, such as water, toluene, or cyclohexane. The amount of solvent that can be used in this feed mixture can vary widely. The ratio of BHMT to BHMT plus solvent can vary from about 0.1 to about 1.0. The preferred optional solvent is water. Furthermore, an optional carrier gas, such as methane, ammonia, hydrogen, nitrogen, or an inert gas, such as those of Group VIIIA of the Periodic Table, may be used. The amount of carrier gas can also vary widely but is usually present in an amount, on a molar basis, of about 0.1 to about 10 times the amount of BHMT. Hydrogen, water, and ammonia participate in the reaction, e.g., hydrogen reduces the ratio of 3,4,5,6-tetrahydro-2,4-azepine to hexamethyleneimine, and water and ammonia appear to keep the catalyst clean and thereby improve catalyst life.

Supported metal catalysts suitable for use in this process comprise a substrate support having dispersed metal on its surface. The metal catalyst comprises palladium, platinum, rhodium, iridium, ruthenium, nickel, or mixtures thereof. The substrate can be carbon, alumina, titania, silica, clays or similar supports known to those skilled in the art. The metal content of the supported catalyst can range from about 0.1% to about 10% by weight, preferably from about 0.5% to about 2% by weight. The metal need not completely coat the substrate; finely dispersed particles of metal on the substrate are satisfactory. The preferred catalyst is palladium on $Al_2O_3$. Liquid samples are collected and analyzed by GC. Depending upon the catalyst and reaction conditions employed, at times low levels or essentially no hexamethylenediamine or N-(6-aminohexyl)hexamethyleneimine are generated.

The present invention further provides a process for the preparation of hexamethyleneimine (HMI), hexamethylenediamine (DMD), and N-(6-aminophenyl)-hexamethyleneimine (AHI) by a (liquid phase) slurry reaction, in either a batch or continuous mode, comprising heating bis(hexamethylene)triamine (BHMT) in the presence of a catalyst comprising palladium, platinum, rhodium, iridium, ruthenium, nickel or mixtures thereof, on a support, or in the presence of a catalyst comprising unsupported palladium black. A mixture of BHMT, catalyst, and an optical solvent, is stirred and heated under a blanked of methane, ammonia, hydrogen, nitrogen, or an inert gas such as those of Group VIII A of the Periodic Table. Samples are periodically withdrawn and analyzed by GC.

The metal catalyst is comprised of palladium, platinum, rhodium, iridium, ruthenium, or nickel or mixtures thereof on a support, or unsupported palladium black. Such catalyst supports are well known in the art and include, for example, carbon, alumina, titania, silica, and clays. The concentration of the metal on the support is from about 0.5% to about 10% by weight. The preferred catalyst is unsupported palladium black.

Operable solvents include benzene substituted with from one to five methyl groups, e.g., toluene, 1,2,4-trimethylbenzene, pentamethylbenzene, and biphenyl. The reaction is most conveniently run at the reflux temperature of the solvent, e.g., toluene boils at about 110° C. and biphenyl at about 225° C. (at atmospheric pressure). The temperature can range from about 100° C. to about 275° C., and the preferred range is from about 175° C. to about 225° C.

Pressures suitable for use in this process are in the range of from about 1 to 70 atm ($1 \times 10^5$ to $7 \times 10^6$ Pascals). Reaction times are typically in the range of from about 1 minute to greater than about 7 hours. Preferably the reaction time ranges from about 10 minutes to about 60 minutes.

The processes of the present invention are useful for the preparation of hexamethyleneimine, hexamethylenediamine, and N-(6-aminohexyl)hexamethyleneimine. Hexamethyleneimine is useful as a synthetic intermediate for the preparation of pharmaceutical, agricultural, and rubber chemicals. Herbicides, such as S-α-naphthylmethyl hexahydro-1H-azepine-1-carbothioate, have been made from it. Hexamethylenediamine is a well-known intermediate in the preparation of nylon-66, and N-(6-aminohexyl)hexamethyl-eneimine is useful as a urethane curing agent.

EXAMPLES

Product analysis was done using a Hewlett Packard 5890 gas chromatograph (GC), equipped with a DB-1701 megabore column (30 m long, 0.53 mm ID, 1 μm film thickness) and a flame-ionization detector. The temperature program was 80° C. for 0 min+8°/min to 250° C. and hold.

Abbreviations used in the tables are as follows: Hex=hexylamine; HMI=hexamethyleneimine; THA=3,4,5,6-tetrahydro-2H-azepin; HMD=hexamethylenediamine; AHI=N-(6-aminohexyl)hexamethyleneimine; BHMT=bis(hexamethylene)triamine; xylene=mixed isomers of dimethylbenzene; cymene=p-isopropyltoluene; durene=1,2,4,5-tetramethylbenzene; 1,2,4-TMB=1,2,4-trimethylbenzene; Me5Ph=pentamethylbenzene.

General Procedure—Fixed-Bed Reaction

A 1 cm (diameter) by 10 cm (length) Vycor® reactor was placed in a tube furnace. A designated quantity of catalyst was charged to the reactor, which was then heated and purged with $N_2$. BHMT, along with any other optional carrier gases and solvents, was passed through a preheat zone and then passed over the catalyst at the designated temperature, flow rate, and pressure. The reactor effluent was collected at room temperature and analyzed by GC.

General Procedure—Slurry Reaction

A mixture of BHMT, catalyst, and optional solvent in a round-bottom flask was heated and stirred under nitrogen. Periodically, samples were withdrawn and analyzed by GC.

EXAMPLE 1

A charge of 0.5 g 0.5% $Pd/Al_2O_3$ placed in a Vycor® reactor, heated to 200° C., was purged with $N_2$ followed by an $H_2$ purge (see Table 1). A saturated solution of BHMT in $H_2O$ was fed at 1 mL/h along with 10 mL/min $H_2$ gas. After running for about 0.5 h, a sample was collected for analysis. Of the fourteen materials analyzed, the major components and their area percents were: BHMT 33%, AHI 7.4%, HMD 37%, and HMI 22% (see Table 2).

EXAMPLES 2-58

Additional examples of the fixed bed reaction were conducted as in Example 1. Table 1 list the catalysts and amounts, solvents, concentration of starting material, and reaction conditions employed. Table 2 lists the resulting products and their amounts.

EXAMPLE 59

A mixture of 2 g BHMT, 20 mL xylene, and 1 g palladium black was refluxed under $N_2$ in a 50 ml round bottom flask (see Table 3). After 60 min a sample was removed and analyzed by gas chromatography. Of the fourteen materials analyzed, the major components and their area percents are: BHMT 39%, AHI 24%, HMD 13%, and HMI 18%. After 180 min (see Table 4) the analysis showed BHMT 6.7%, AHI 39%, HMD 6.8%, and HMI 39%.

EXAMPLES 60-94

Additional examples of the (liquid phase) slurry reaction were conducted as in Example 60 using the catalyst and amount, starting material amounts, solvents and amounts, and reaction conditions as shown in Table 3. Table 4 lists the resulting products and their amounts.

TABLE 1

| | Fixed-Bed Catalyst: Reaction Conditions | | | | | | | |
|---|---|---|---|---|---|---|---|---|
| Example | Catalyst | Weight g | Solvent | Ratio BHMT/Solvent | Temp °C. | Liq. Flow mL/h | Gas | Gas Flow mL/min |
| 1 | 0.5% $Pd/Al_2O_3$ | 0.5 | water | 1 | 200 | 1 | $H_2$ | 10 |
| 2 | 0.5% $Pd/Al_2O_3$ | 3.0 | water | 1 | 200 | 1 | $N_2$ | 10 |
| 3 | 0.5% $Pd/Al_2O_3$ | 3.0 | water | 1 | 200 | 2 | — | — |
| 4 | 0.5% $Pd/Al_2O_3$ | 3.0 | water | 1 | 200 | 1 | $N_2$ | 10 |
| 5 | 0.5% $Pd/Al_2O_3$ | 3.0 | water | 1 | 200 | 1 | $N_2$ | 5 |
| 6 | 0.5% $Pd/Al_2O_3$ | 3.0 | water | 1 | 150 | 0.5 | $N_2$ | 5 |
| 7 | 0.5% $Pd/Al_2O_3$ | 3.0 | water | 1 | 150 | 2 | $N_2$ | 5 |
| 8 | 0.5% $Pd/Al_2O_3$ | 3.0 | water | 1 | 250 | 0.5 | $N_2$ | 5 |
| 9 | 0.5% $Pd/Al_2O_3$ | 3.0 | water | 1 | 250 | 2 | $N_2$ | 5 |
| 10 | 0.5% $Pd/Al_2O_3$ | 3.0 | water | 1 | 200 | 1 | $N_2$ | 5 |
| 11 | CG-21 0.5% Pd/C | 3.5 | water | 1 | 250 | 2 | $H_2$ | 10 |

TABLE 1-continued

Fixed-Bed Catalyst: Reaction Conditions

| Example | Catalyst | Weight g | Solvent | Ratio BHMT/Solvent | Temp °C. | Liq. Flow mL/h | Gas | Gas Flow mL/min |
|---|---|---|---|---|---|---|---|---|
| 12 | CG-21 0.5% Pd/C | 3.5 | water | 1 | 150 | 2 | $H_2$ | 10 |
| 13 | 0.2% Pd/SiO$_2$ | 4.4 | water | 1 | 200 | 2 | $H_2$ | 10 |
| 14 | 2.0% Pd/TiO$_2$ | 4.6 | water | 1 | 200 | 2 | $H_2$ | 10 |
| 15 | 0.5% Ru/C | 2.3 | water | 1 | 200 | 2 | $H_2$ | 10 |
| 16 | 0.5% Pd/C | 3.5 | toluene | 0.5 | 200 | 2 | $N_2$ | 10 |
| 17 | 0.5% Pd/C | 3.5 | toluene | 0.5 | 200 | 2 | $H_2$ | 10 |
| 18 | 0.5% Pt/Al$_2$O$_3$ | 3.0 | water | 1 | 200 | 2 | $H_2$ | 10 |
| 19 | NI-1430 | 4.1 | water | 1 | 200 | 2 | $N_2$ | 10 |
| 20 | NI-1430 | 4.1 | water | 1 | 200 | 2 | $H_2$ | 10 |
| 21 | 2% Ru/Al$_2$O$_3$ | 4.9 | water | 1 | 200 | 2 | $H_2$ | 10 |
| 22 | 0.5% Pd/Kaolin | 3.7 | water | 1 | 200 | 2 | $H_2$ | 10 |
| 23 | 0.5% Pd/C CG-21 | 3.5 | water | 1 | 200 | 2 | $H_2$ | 10 |
| 24 | 0.5% Pd/C CG-21 | 3.5 | water | 1 | 200 | 2 | $H_2$ | 50 |
| 25 | 0.5% Pd/C CG-21 | 3.5 | water | 1 | 220 | 2 | $H_2$ | 10 |
| 26 | 0.5% Pd/C CG-21 | 3.5 | water | 1 | 200 | 2 | $H_2$ | 5 |
| 27 | 0.5% Pd/Al$_2$O$_3$ | 0.5 | water | 1 | 200 | 2 | $H_2$ | 10 |
| 28 | 0.5% Pd/Al$_2$O$_3$ | 0.5 | water | 1 | 200 | 3 | $H_2$ | 10 |
| 29 | 0.5% Pd/Al$_2$O$_3$ | 2.0 | water | 1 | 200 | 3 | $H_2$ | 10 |
| 30 | 0.5% Pd/Al$_2$O$_3$ | 2.0 | water | 1 | 200 | 1 | $H_2$ | 10 |
| 31 | 0.5% Pd/Al$_2$O$_3$ | 2.0 | water | 1 | 200 | 2 | $H_2$ | 10 |
| 32 | 0.5% Pd/Al$_2$O$_3$ | 8.0 | water | 1 | 200 | 3 | $H_2$ | 10 |
| 33 | 0.5% Pd/Al$_2$O$_3$ | 8.0 | water | 1 | 200 | 1 | $H_2$ | 10 |
| 34 | 0.5% Pd/Al$_2$O$_3$ | 8.0 | water | 1 | 200 | 2 | $H_2$ | 10 |
| 35 | 0.5% Pd/Al$_2$O$_3$ | 8.0 | water | 1 | 220 | 1 | $H_2$ | 10 |
| 36 | 0.5% Pd/Hy zeolite | 2.0 | water | 1 | 200 | 1 | $H_2$ | 10 |
| 37 | 0.5% Pd/Hy zeolite | 2.0 | water | 1 | 200 | 2 | $H_2$ | 10 |
| 38 | 0.5% Pd/SiO$_2$ | 0.5 | water | 1 | 200 | 2 | $H_2$ | 10 |
| 39 | 0.5% Pd/SiO$_2$ | 0.5 | water | 1 | 200 | 3 | $H_2$ | 10 |
| 40 | 0.5% Pd/SiO$_2$ | 0.5 | water | 1 | 200 | 4 | $H_2$ | 10 |
| 41 | 0.5% Pd/SiO$_2$ | 2.0 | water | 1 | 200 | 1 | $H_2$ | 10 |
| 42 | 0.5% Pd/SiO$_2$ | 2.0 | water | 1 | 200 | 2 | $H_2$ | 10 |
| 43 | 0.5% Pd/SiO$_2$ | 2.0 | water | 1 | 200 | 4 | $H_2$ | 10 |
| 44 | 40% Ni/Al$_2$O$_3$ | 5.0 | water | 1 | 100 | 1 | $H_2$ | 10 |
| 45 | 40% Ni/Al$_2$O$_3$ | 5.0 | water | 1 | 120 | 1 | $H_2$ | 10 |
| 46 | 40% Ni/Al$_2$O$_3$ | 5.0 | water | 1 | 140 | 1 | $H_2$ | 10 |
| 47 | 40% Ni/Al$_2$O$_3$ | 5.0 | water | 1 | 160 | 1 | $H_2$ | 10 |
| 48 | 40% Ni/Al$_2$O$_3$ | 5.0 | water | 1 | 160 | 2 | $H_2$ | 10 |
| 49 | 40% Ni/Al$_2$O$_3$ | 5.0 | water | 1 | 160 | 4 | $H_2$ | 10 |
| 50 | 0.5% Pd/Al$_2$O$_3$ | 0.5 | water | 1 | 140 | 1 | $H_2$ | 10 |
| 51 | 0.5% Pd/Al$_2$O$_3$ | 0.5 | water | 1 | 115 | 1 | $H_2$ | 10 |
| 52 | 0.5% Pd/Al$_2$O$_3$ | 0.5 | water | 1 | 200 | 1 | $H_2$ | 10 |
| 53 | 0.5% Pd/Al$_2$O$_3$ | 0.5 | water | 1 | 220 | 1 | $H_2$ | 10 |
| 54 | 0.5% Pd/Al$_2$O$_3$ | 0.5 | water | 1 | 240 | 1 | $H_2$ | 10 |
| 55 | 0.5% Pd/Al$_2$O$_3$ | 0.5 | water | 1 | 260 | 1 | $H_2$ | 10 |
| 56 | 0.05% Pd/Al$_2$O$_3$ | 5.0 | water | 1 | 200 | 1 | $H_2$ | 10 |
| 57 | 0.05% Pd/Al$_2$O$_3$ | 5.0 | water | 1 | 225 | 2 | $H_2$ | 10 |
| 58 | 0.05% Pd/Al$_2$O$_3$ | 5.0 | water | 1 | 250 | 4 | $H_2$ | 10 |

TABLE 2

Fixed-bed Catalyst: Products
GC Area Percent

| Example | Hex | HMI | THA | HMD | AHI | BHMT |
|---|---|---|---|---|---|---|
| 1 | 0 | 22 | 0.26 | 37 | 7.4 | 33 |
| 2 | 6.6 | 90 | 1.12 | 1.4 | 0.71 | 0.59 |
| 3 | 3.1 | 68 | 2.7 | 11 | 4.3 | 11 |
| 4 | 2.7 | 73 | 8.5 | 9.9 | 2.6 | 2.9 |
| 5 | 3.8 | 76 | 6.2 | 7.9 | 2.3 | 8.0 |
| 6 | 0.33 | 13 | 0.7 | 1.5 | 0.30 | 0.87 |
| 7 | 0.08 | 11 | 1.2 | 9.8 | 0.99 | 3.0 |
| 8 | 0.83 | 36 | 7.5 | 5.8 | 2.3 | 17.1 |
| 9 | 0.65 | 32 | 17.8 | 23 | 8.4 | 52 |
| 10 | 0.34 | 41 | 5.7 | 19 | 8.2 | 26 |
| 11 | 0.34 | 0 | 0.10 | 0.59 | 0.01 | 0.05 |
| 12 | 0 | 0.35 | 0.55 | 0 | 0.06 | 0.03 |
| 13 | 0.55 | 31 | 1.8 | 37 | 13 | 15 |
| 14 | 4.2 | 92 | 0.46 | 0.63 | 0.55 | 1.0 |
| 15 | 0.29 | 27 | 1.7 | 28 | 19 | 21 |
| 16 | 0.66 | 51 | 6.5 | 25 | 11 | 3.8 |
| 17 | 1.0 | 72 | 0.28 | 14 | 7 | 2.7 |
| 18 | 2.0 | 80 | 0.54 | 6.1 | 4.7 | 2.5 |
| 19 | 0.13 | 23 | 3.0 | 8.5 | 34 | 26 |
| 20 | 0.18 | 34 | 1.6 | 7.5 | 37 | 16 |
| 21 | 1.0 | 88 | 0.33 | 0 | 3.4 | 2.3 |
| 22 | 1.6 | 61 | 0.72 | 11 | 5.6 | 19 |
| 23 | 1.1 | 77 | 0.33 | 14 | 4.0 | 1.6 |
| 24 | 1.1 | 77 | 0.32 | 14 | 4.2 | 1.7 |
| 25 | 1.0 | 11 | 1.0 | 11 | 5.8 | 3.9 |
| 26 | 0.54 | 65 | 0.58 | 22 | 7.6 | 2.4 |
| 27 | 0 | 9.6 | 0.44 | 13 | 3.2 | 74 |
| 28 | 0 | 4.6 | 0.63 | 12 | 3.3 | 79 |
| 29 | 0.80 | 37 | 0.74 | 19 | 3.9 | 38 |
| 30 | 1.4 | 65 | 0.41 | 13 | 6.8 | 12 |
| 31 | 1.0 | 57 | 0.63 | 20 | 6.4 | 14 |
| 32 | 3.3 | 50 | 2.5 | 28 | 2.1 | 14 |
| 33 | 2.1 | 71 | 2.5 | 8.6 | 3.1 | 12 |
| 34 | 1.62 | 66 | 0.84 | 10 | 4.6 | 16 |
| 35 | 5.7 | 60 | 0.57 | 1.2 | 3.1 | 28 |
| 36 | 0.15 | 49 | 0.14 | 37 | 2.8 | 10 |
| 37 | 0.27 | 58 | 0.13 | 35 | 2.2 | 4.3 |
| 38 | 0 | 4.5 | 0.33 | 11 | 2.8 | 81 |
| 39 | 0 | 2.7 | 0.47 | 6.5 | 1.8 | 88 |
| 40 | 0 | 2.0 | 0.58 | 5.3 | 1.4 | 90 |
| 41 | 2.1 | 89 | 0.11 | 6.2 | 1.1 | 1.6 |
| 42 | 1.9 | 68 | 0.35 | 23 | 3.3 | 2.1 |
| 43 | 0.65 | 49 | 0.90 | 36 | 5.9 | 6.6 |
| 44 | | 1.8 | 0.42 | 0.61 | 5.0 | 90 |

TABLE 2-continued

Fixed-bed Catalyst: Products GC Area Percent

| Example | Hex | HMI | THA | HMD | AHI | BHMT |
|---|---|---|---|---|---|---|
| 45 |  | 1.2 | 0.22 | 1.0 | 7.5 | 83 |
| 46 |  | 5.3 | 0.11 | 2.7 | 16 | 67 |
| 47 |  | 23 | 0.00 | 3.7 | 31 | 37 |
| 48 |  | 10 | 0.19 | 2.4 | 20 | 63 |
| 49 |  | 1.9 | 0.43 | 1.1 | 6.8 | 88 |
| 50 | 0 | 10 | 0.24 | 20 | 2.5 | 66 |
| 51 | 0 | 0.26 | 0.49 | 1.8 | 1.2 | 95 |
| 52 | 0.50 | 96 | 0 | 0.91 | 0.57 | 1.1 |
| 53 | 0.89 | 98 | 0.14 | 0.11 | 0 | 0.28 |
| 54 | 0.39 | 99 | 0.17 | 0 | 0 | 0.24 |
| 55 | 0.24 | 98 | 0.33 | 0 | 0 | 0.46 |
| 56 | 0.93 | 78 | 0.41 | 16 | 2.3 | 1.91 |
| 57 | 5.4 | 90 | 0.58 | 3.1 | 0.77 | 0.32 |
| 58 | 0.63 | 36 | 8.2 | 36 | 11 | 6.5 |

TABLE 3

Slurry Catalyst: Reaction Conditions

| Example | Catalyst | Weight g | BHMT g | Solvent | Volume mL | Temp °C. | Time min |
|---|---|---|---|---|---|---|---|
| 59 | Pd-Black | 1.0 | 2 | xylene | 20 | 140 | 180 |
| 60 | 1% Pd/C | 1 | 2 | xylene | 20 | 140 | 120 |
| 61 | Pd-Black | 1 | 2 | xylene | 20 | 140 | 120 |
| 62 | Pd-Black | 0.05 | 2 | xylene | 20 | 140 | 120 |
| 63 | 5% Ru/C | 1 | 2 | xylene | 20 | 140 | 120 |
| 64 | 5% Pt/C #26 | 1 | 2 | xylene | 20 | 140 | 120 |
| 65 | Pd/Si—Al—O #57 | 1 | 2 | xylene | 20 | 140 | 120 |
| 66 | Pd/Al$_2$O$_3$ #23 | 1 | 2 | xylene | 20 | 140 | 120 |
| 67 | 5% Pd/0.05% Pt/C #49 | 1 | 2 | xylene | 20 | 140 | 120 |
| 68 | 5% Pd/C | 1 | 4.85 | xylene | 20 | 140 | 300 |
| 69 | 5% Pd/C | 1 | 2 | cymene | 20 | 176 | 180 |
| 70 | 5% Ru/C | 1 | 5.1 | xylene | 20 | 140 | 240 |
| 71 | Pd-Black | 0.2 | 2 | xylene | 20 | 140 | 1350 |
| 72 | Pd/SiO$_2$—Al$_2$O$_3$ | 1.0 | 2 | xylene | 20 | 140 | 420 |
| 73 | Pd | 0.2 | 2 | xylene | 20 | 140 | 60 |
| 74 | Pd | 1.0 | 2 | toluene | 20 | 110 | 420 |
| 75 | Pd | 0.02 | 2.0 | none | — | 140 | 120 |
| 76 | 5% Pd/C | 1.0 | 2.0 | none | — | 140 | 120 |
| 77 | Pd | 0.1 | 2.0 | xylene | 10 | 140 | 45 |
| 78 | 5% Pd/C | 1.0 | 2.0 | 1,2,4-TMB | 10 | 168 | 30 |
| 79 | 5% Pd/C | 1.0 | 2.0 | durene | 10 | 195 | 8 |
| 80 | 5% Pd/C | 0.01 | 2.0 | durene | 10 | 195 | 60 |
| 81 | 10% Pd/C | 0.05 | 1.0 | 1,2,4-TMB | 5 | 168 | 60 |
| 82 | 4.3% Pd/Al$_2$O$_3$ | 1.16 | 1.0 | 1,2,4-TMB | 5 | 168 | 60 |
| 83 | 5% Pd/C | 1.0 | 1.0 | 1,2,4-TMB | 5 | 168 | 60 |
| 84 | Pd | 0.05 | 1.0 | 1,2,4-TMB | 5 | 168 | 60 |
| 85 | Pd | 0.05 | 1.0 | 1,2,4-TMB | 20 | 168 | 60 |
| 86 | Pd | 0.05 | 1.0 | 1,2,4-TMB | 5 | 168 | 60 |
| 87 | Pd | 0.05 | 1.0 | 1,2,4-TMB | 1 | 168 | 30 |
| 88 | 20% Pd/Peat Carbon | 0.25 | 1.0 | 1,2,4-TMB | 5 | 168 | 60 |
| 89 | 20% Pd/Wood Carbon | 0.25 | 1.0 | 1,2,4-TMB | 5 | 168 | 60 |
| 90 | 5% Rh/C | 1.0 | 1.0 | 1,2,4-TMB | 5 | 168 | 60 |
| 91 | 5% Ru/C | 1.0 | 1.0 | 1,2,4-TMB | 5 | 168 | 60 |
| 92 | Ru | 0.05 | 1.0 | 1,2,4-TMB | 5 | 168 | 120 |
| 93 | Pd | 0.01 | 1.0 | Me$_5$Ph | 5 | 231 | 60 |
| 94 | Pd | 0.05 | 1.0 | biphenyl | 5 | 255 | 20 |

TABLE 4

Slurry Catalyst: Products GC Area Percent

| Example | Hex | HMI | THA | HMD | AHI | BHMT |
|---|---|---|---|---|---|---|
| 59 |  | 39 | 4.4 | 6.8 | 39 | 6.7 |
| 60 |  | 1.1 | 1.2 | 5.1 | 1.8 | 90 |
| 61 |  | 18 | 1.4 | 19 | 23 | 37 |
| 62 |  | 3.8 | 0.78 | 6.1 | 3.3 | 86 |
| 63 |  | 2.2 | 0.10 | 1.8 | 7.7 | 84 |
| 64 |  | 3.4 | .67 | 5.9 | 2.6 | 82 |
| 65 |  | 22 | 2.4 | 23 | 26 | 24 |
| 66 |  | 7.8 | 4.4 | 12 | 6.4 | 67 |
| 67 |  | 14 | 1.74 | 27 | 12 | 42 |
| 68 |  | 17 | 2.7 | 19 | 20 | 40 |
| 69 |  | 85 | 14 | 0 | 0.58 | 0 |
| 70 |  | 2.2 | 0.10 | 1.8 | 7.7 | 84 |
| 71 |  | 22 | 2.3 | 15 | 31 | 26 |
| 72 |  | 16 | 2.4 | 24 | 15 | 39 |
| 73 |  | 23 | 2.8 | 1.4 | 24 | 17 |
| 74 |  | 42 | 2.5 | 6.9 | 37 | 7.3 |
| 75 |  | 20 | 4.7 | 16 | 31 | 23 |
| 76 |  | 4.7 | 2.3 | 37 | 4.5 | 47 |
| 77 |  | 2.6 | 1.6 | 4.5 | 2.3 | 88 |
| 78 |  | 7.5 | 2.1 | 13 | 7.7 | 70 |
| 79 |  | 18 | 3.5 | 23 | 13 | 42 |
| 80 |  | 16 | 3.5 | 27 | 22 | 31 |
| 81 | 8.4 | 42 | 4.2 | 5.6 | 34 | 9.4 |
| 82 | 0 | 16 | 2.2 | 22 | 14 | 45 |
| 83 | 6.2 | 41 | 0 | 0 | 29 | 18 |
| 84 | 3.5 | 29 | 4.6 | 15 | 29 | 18 |
| 85 |  | 6.7 | 3.6 | 8.8 | 8.6 | 72 |
| 86 |  | 29 | 4.6 | 15 | 29 | 18 |
| 87 |  | 18 | 3.5 | 23 | 13 | 42 |
| 88 | 6.4 | 34 | 4.1 | 3.8 | 37 | 8.7 |
| 89 | 4.0 | 37 | 3.8 | 5.1 | 37 | 8.5 |
| 90 | 0 | 23 | 2.1 | 3.5 | 48 | 18 |
| 91 | 0 | 2.0 | 0.73 | 4.0 | 5.5 | 76 |
| 92 |  | 0 | 1.4 | 1.7 | .53 | 96 |
| 93 |  | 17 | 4.1 | 21 | 13 | 45 |
| 94 |  | 40 | 7.4 | 7.7 | 33 | 6.4 |

I claim:

1. A process for the preparation of hexamethyleneimine, hexamethylenediamine and N-(6-aminohexyl)-hexamethyleneimine comprising pyrolyzing bis(hexamethylene)-triamine in the presence of a fixed bed catalyst or a slurry catalyst comprising palladium, platinum, ruthenium, iridium, rhodium, or nickel on a support, wherein said process is conducted at a temperature of from about 100° C. to about 275° C. and at a pressure of from about $1 \times 10^5$ to about $7 \times 10^6$ Pascals.

2. The process of claim 1 wherein bis(hexamethylene)triamine is pyrolyzed in the presence of a fixed bed catalyst.

3. The process of claim 1 wherein bis(hexamethylene)triamine is pyrolyzed in the presence of a slurry catalyst.

4. The process of claim 1 conducted at a temperature of from about 175° C. to about 225° C.

5. The process of claims 2 or 3 wherein the support comprises carbon, alumina, titania, silica or clays.

6. The process of claim 5 wherein the metal content of the supported catalyst is from about 0.1 to about 10% by weight.

7. The process of claim 2 conducted in a solvent comprising water, toluene, or cyclohexane.

8. The process of claim 2 conducted in a carrier gas comprising methane, ammonia, hydrogen, nitrogen or an inert gas of Group VIIIA of the Periodic Table.

9. The process of claim 3 conducted in a solvent comprising benzene substituted with 1 to 5 methyl groups.

10. The process of claim 9 wherein the solvent is xylene or 1,2,4-trimethylbenzene.

11. The process of claim 10 conducted at the reflux temperature of the solvent.

12. The process of claim 3 conducted under a blanket of methane, nitrogen, hydrogen or an inert gas of Group VIII A of the Periodic Table.

13. The process of claim 2 wherein the catalyst is palladium on $Al_2O_3$.

14. The process of claim 3 in the presence of an unsupported catalyst comprising palladium black.

* * * * *